(12) United States Patent
Yoon

(10) Patent No.: US 8,278,080 B2
(45) Date of Patent: Oct. 2, 2012

(54) METHOD FOR PRETREATING BIOMASS TO PRODUCE BIOETHANOL

(75) Inventor: Kyung Pyo Yoon, Daegu (KR)

(73) Assignee: Industry Academic Cooperation Foundation Keimyung University, Daegu (KR)

( * ) Notice: Subject to any disclaimer, the term of this patent is extended or adjusted under 35 U.S.C. 154(b) by 0 days.

(21) Appl. No.: 13/319,539

(22) PCT Filed: Jan. 18, 2010

(86) PCT No.: PCT/KR2010/000290
§ 371 (c)(1),
(2), (4) Date: Nov. 9, 2011

(87) PCT Pub. No.: WO2010/131829
PCT Pub. Date: Nov. 18, 2010

(65) Prior Publication Data
US 2012/0052543 A1 Mar. 1, 2012

(30) Foreign Application Priority Data
May 14, 2009 (KR) ........................ 10-2009-0042121

(51) Int. Cl.
*C12P 7/06* (2006.01)
*C12P 7/14* (2006.01)
(52) U.S. Cl. ........................................ 435/161; 435/162

(58) Field of Classification Search ................... 435/72, 435/161, 162
See application file for complete search history.

(56) References Cited

U.S. PATENT DOCUMENTS

| | | | |
|---|---|---|---|
| 6,333,181 B1 | 12/2001 | Ingram et al. | |
| 7,504,245 B2 | 3/2009 | Kinley et al. | |
| 2010/0297704 A1* | 11/2010 | Li | ................................. 435/72 |

OTHER PUBLICATIONS

International Search Report from PCT/KR2010/000290, dated Oct. 7, 2010 (date of completion of search) and Oct. 8, 2010 (date of mailing of report).

* cited by examiner

*Primary Examiner* — Maryam Monshipouri
(74) *Attorney, Agent, or Firm* — Clark & Elbing LLP

(57) ABSTRACT

Disclosed is a method for preparing bioethanol from biomass. The feedstock for preparation of bioethanol, i.e. the biomass, is pretreated by a combination of chemical and physical methods. The method is advantageous in that detoxification is unnecessary since the substances that inhibit fermentation are not produced and acid reconcentration for recycling is not needed. Further, since the sonication makes saccharification easier, removal of lignin (delignification), which interferes with the saccharification of cellulose, is unnecessary. Accordingly, the present disclosure allows to produce bioethanol with high yield and at low cost in an environment-friendly manner.

13 Claims, 19 Drawing Sheets 1.5% H₂SO₄, 130℃ 40min

Sonication and French press

Easy penetration of cellulase through the disrupted cellulose structure

METHOD FOR PRETREATING BIOMASS TO PRODUCE BIOETHANOL

CROSS REFERENCE TO RELATED APPLICATIONS

This application is the U.S. national stage filing under 35 U.S.C. §371 of international Application PCT/KR2010/000290, filed Jan. 18, 2010, which claimed benefit of Korean Patent Application 10-2009-0042121, filed May 14, 2009.

TECHNICAL FIELD

The present disclosure relates to a method for preparing bioethanol from biomass, more particularly to a method for preparing bioethanol from biomass including pretreating biomass chemically and physically and thus not requiring detoxification, sulfuric acid reconcentration, recycling and delignification processes.

BACKGROUND

A lot of attempts are being made to develop a technology for converting biomass for commercial production of bioethanol as a renewable energy source. Worldwide, ethanol is mostly produced by fermentation, accounting for up to 90% of ethanol produced globally. Although most bioethanol is produced from sugar cane (Brazil) or molasses and corn (the United States), other starch materials such as wheat, barley and rye are also suitable to be used. The starch-containing grains have to be converted into sugar. In Europe, starch grains (e.g., wheat) and sugar beet are the major source of bioethanol production.

The fermentation of sugar into ethanol is a large-scale technology that has been developed for commercial purposes. The fermentation technology has been developed and optimized for thousands of years. The cost for the fermentation is largely dependent on the price of the biomass source and may account for 55-80% of the final price of ethanol. Brazil and the United States produce the majority of bioethanol consumed globally, and the global demand on bioethanol is increasing abruptly. This inevitably increases the price of corn, sugar cane and other important grains.

The starch-containing grain is subjected as milling or grinding in order to release starch. Then, it is diluted in water and then cooked to dissociate all water-soluble starches. At the same time, the starch is converted into sugar. This process may be carried out by enzymatic or acid hydrolysis. In acid hydrolysis, diluted mineral acid is added to the grain slurry before cooking. The resultant short carbohydrates may be fermented by microorganisms such as yeast. Ethanol is produced through the fermentation, and the ethanol may be concentrated through a series of distillation and dehydration procedures. Sugar is converted to ethanol as a result of the fermentation process.

Other plant sources may also be a good source of sugar. Actually, the selection of the plant source depends not only on what plant grows well in the particular region but also on the sugar content and availability of the plant. New promising techniques will allow more practicable production of ethanol. The plants sources for producing ethanol from the stem, roots or leaves of plants rather than from the kernel of corn are known as cellulosic material. The so-called cellulose ethanol has been known from several years ago, but it is regarded as ineffective and expensive to break down cellulose by fermentation. The recent technical advancement as well as high oil price provides a more competitive edge. However, many people still agree that more progress in technology is required to reduce the current production cost.

Plant cell walls are composed of lignocellulosic materials, which are represented by cellulose (linear glucose polymers), hemicellulose (highly branched heteropolymers) and lignin (crosslinked aromatic macromolecules with large molecular weight). The bonding between the polysaccharide components (cellulose and hemicellulose) and non-polysaccharide components (lignin) is the main cause of mechanical and biological resistance. Cellulose, the most abundant polysaccharide on earth, is a polymer accounting for 50% or more of the wood weight wherein cellobiose (D-glucopyranosyl-β-1, 4-D-glucopyranose) is arranged in good order. The cellulose chain which forms fibrils consists of about 10,000 glucose units. The cellulosic material has a crystal domain separated from the less-ordered, amorphous domain, which allows chemical and biochemical attack. Cellulases can hydrolyze the cellulose polymer to monomers, and the resulting glucose is fermented into ethanol by the yeast *Saccharomyces cerevisiae*. Accordingly, the biocatalysis is at the center of the biomass ethanol technology. Hemicellulose consists of cellulose and lignin. Hemicellulose in wood is a short (100-200 sugar units), highly-branched heteropolymer consisting of the predominant xylose as well as glucose, mannose, galactose, arabinose and other uronic acids. $C_5$ and $C_6$ sugars are linked by 1,3-, 1,6- or 1,4-glucosidic linkages, which differentiate cellulose from lignin, and are often acetylated. Lignin is a 3-dimensional polyphenolic network of dimethoxylated, monomethoxylated and non-methoxylated phenylpropanoid units, derived from p-hydroxycinnamyl alcohol. Lignin is hydrophobic and highly resistant to chemical and biological degradation. Cellulosic fibrils are embedded in an amorphous matrix network of hemicellulose and lignin, and they serve as glues between the plant cells, providing resistance to biodegradation. Other non-structural components (phenols, tannins, fats, sterols, sugars, starches, proteins and ashes) of the plant tissue generally accounts for 5% or less of the dry weight of wood.

In order to hydrolyze the biomass polysaccharides into fermentable sugars, for example by depolymerization, such pretreatment processes as steam explosion, mild acid treatment, strong acid treatment, ammonia treatment, hydroxide treatment, etc. are employed. No matter what it is, the pretreatment process should be environment-friendly and economically feasible. The pretreatment method will be selected considering process dependency and cost, as well as process yield and production parameters.

The present disclosure presents a method for producing new renewable energy allowing to cope with the global climate change by removing carbon dioxide from the atmosphere by photosynthesis, without affecting the global grain prices. And, the by-product produced during bioethanol production may be used as livestock feed additives, fuels for steam and power generation, raw materials of gypsum board, cement additives, fertilizers, or the like. Thus, the present disclosure provides a method for utilizing non-food biomass from corn stover, rice straw, wheat straw, fruit skin, sugar cane stalk or sorghum stalk, which are available in large scale at low cost, 100% as a valuable resource.

Throughout the specification, a number of publications and patent documents are referred to and cited. The disclosure of the cited publications and patent documents is incorporated herein by reference in its entirety to more clearly describe the state of the related art and the present disclosure.

DETAILED DESCRIPTION OF THE INVENTION

The inventors of the present disclosure have made efforts to prepare bioethanol from biological resources using an environment-friendly and inexpensive process. As a result, they have found out that bioethanol can be produced with high yield via using an environment-friendly and inexpensive process requiring no detoxification or delignification by chemically acid hydrolyzing biomass and then carrying out sonication alone or in combination with French pressing.

The present disclosure is directed to providing a method for preparing bioethanol from non-food biomass.

Other features and aspects will be apparent from the following detailed description, drawings, and claims.

In one general aspect, the present disclosure provides a method for preparing bioethanol from biomass, comprising: (a) pulverizing biomass; (b) hydrolyzing the pulverized biomass by treating with an acid; (c) separating the resultant of the step (b) into liquid and solid phases; (d) (d-1) neutralizing the liquid phase of the resultant of the step (c) by treating with a neutralizer to obtain pentose, or (d-2) sonicating the solid phase of the resultant of the step (c) and treating the same with cellulase to obtain hexose; and (e) fermenting the pentose, hexose, or pentose and hexose of the step (d-1) or (d-2) by treating with ethanol-producing fermenting microorganism.

The inventors of the present disclosure have made efforts to prepare bioethanol from biological resources using an environment-friendly and inexpensive process. As a result, they have found out that bioethanol can be produced with high yield via using an environment-friendly and inexpensive process requiring no detoxification or delignification by chemically acid hydrolyzing biomass and then carrying out sonication alone or in combination with French pressing. The present disclosure presents a method for producing new renewable energy allowing to cope with the global climate change without affecting the global grain prices. And, the by-product produced during bioethanol production may be used as livestock feed additives, fuels for steam and power generation, raw materials of gypsum board, cement additives, fertilizers, or the like. Thus, the present disclosure provides a method for utilizing non-food biomass from corn stover, rice straw, wheat straw, fruit skin, sugar cane stalk or sorghum stalk, which are available in large scale at low cost, 100% as a valuable resource.

Now, the individual steps of the method for preparing bioethanol from biomass according to the present disclosure will be described in detail.

(a) Pulverization of Biomass

First, biomass, which is used as a source of bioethanol, is crushed.

The biomass used as the source material in the present disclosure may include various known biological resources containing cellulose or lignocellulosic materials. Specifically, it may be rice straw, wheat straw, corn cob, corn stover, rice husk, paper, wood, sawdust, agricultural waste, grass, sugar cane bagasse, cotton, flax, bamboo, abaca, algae, fruit skin or seaweed. More specifically, it may be corn stover, rice straw, wheat straw, sorghum stalk, rice husk, wood, sawdust, sugar cane bagasse or fruit skin. Most specifically, it may be corn stover, corn cob, rice straw, wheat straw, sawdust, sorghum stalk, sugar cane bagasse or fruit skin.

The biomass may be pulverized by various physical pulverization methods known in the art, including, for example, shearing, milling or grinding. A mill, knife cutter or mixer may be used to pulverize the biomass.

In a specific embodiment of the present disclosure, the method of the present disclosure may further comprise, between the step (a) and the step (b), (a-1) passing the biomass pulverized in the step (a) through meshes with one side being 0.25-5 mm in length. More specifically, the length of one side of the meshes may be 0.25-3 mm, most specifically 0.25-2 mm.

The reason why the pulverized biomass is passed through the meshes with one side being 0.25-5 mm in length is to increase surface area in order to help tissue softening of the biomass in the following acid hydrolysis and sonication steps.

(b) Acid Hydrolysis of Pulverized Biomass

Next, the physically pulverized biomass is hydrolyzed by treating with an acid.

The acid used to hydrolyze the pulverized biomass may include various acids known in the art. Specifically, it may be sulfuric acid, hydrochloric acid, nitric acid, acetic acid, formic acid or phosphoric acid. More specifically, it may be sulfuric acid, hydrochloric acid or nitric acid. Most specifically, it may be sulfuric acid.

In another specific embodiment of the present disclosure, the hydrolysis in the step (b) may be performed with a 0.1-10% (v/v) acid at 80-150° C. for 20-120 minutes, more specifically with a 0.1-5% (v/v) acid at 100-150° C. for 20-80 minutes, most specifically with a 0.1-2% (v/v) acid at 120-140° C. for 20-60 minutes.

The most prominent feature of the present disclosure is that a low-concentration acid of 10% (v/v) or less is used instead of a high-concentration acid. When a highly concentrated acid is used, it may corrode instruments and a process of concentrating the once-used, diluted acid is required to recycle it. Furthermore, a detoxification process is needed to remove toxic substances and a lot of waste is generated. The use of the low-concentration acid is also advantageous in that the pretreatment can be carried out at relatively low temperature and in short time, thereby saving the energy cost and allowing the production of bioethanol at low cost.

(c) Separation of the Resultant of the Step (b) into Liquid and Solid Phases

After the pulverized biomass is acid hydrolyzed, the resultant is separated into liquid and solid phases.

The resultant of the step (b), which is a mixture solution of liquid and solid phases, may be separated using various known filtration apparatuses. For example, a filter press, a centrifuge, a membrane filter or a nanofilter may be used for the separation.

(d) (d-1) Neutralization of the Liquid Phase in the Resultant of the Step (c) to Obtain Pentose The separated liquid phase is neutralized by adding a neutralizer to obtain pentose.

The neutralizer used in the present disclosure may include various acid-neutralizing neutralizers known in the art. Specifically sodium hydroxide (NaOH), sodium carbonate ($Na_2CO_3$), magnesium hydroxide ($Mg(OH)_2$), slaked lime ($Ca(OH)_2$), quicklime (CaO) or calcium carbonate ($CaCO_3$) may be used. More specifically, sodium hydroxide (NaOH), sodium carbonate ($Na_2CO_3$) or calcium carbonate ($CaCO_3$) may be used. Most specifically, calcium carbonate ($CaCO_3$) may be used. Gypsum ($CaSO_4$), which is formed when sulfuric acid reacts with calcium carbonate ($CaCO_3$), may be used as the raw material of gypsum board, cement additive, fertilizer, or the like.

In a specific embodiment of the present disclosure, the pentose comprises xylose and arabinose.

(d-2) Sonication and Cellulase Treatment of the Solid Phase in the Resultant of the Step (c) to Obtain Hexose The solid phase may be pulverized before sonication.

Before the sonication, the solid phase may be separated using a filter and further pulverized for 5-20 minutes using a mixer in order to increase surface of the solid phase for the sonication and cellulase treatment.

In a specific embodiment of the present disclosure, the pulverized solid phase may have an average particle diameter from 0.1 mm to 2 cm, more specifically from 0.1 mm to 1 cm, further more specifically from 0.1 mm to 0.5 mm, most specifically from 0.1 mm to 0.25 mm.

In the present disclosure, the chemically pretreated (acid hydrolyzed) solid phase is sonicated and then treated with cellulase to obtain hexose. The enzyme treatment residue may be used as livestock feed additive, fuel for steam and power generation, or the like.

During the sonication, bubbles are generated in a medium containing cellulose, which collapse implosively after growing. While the bubbles are collapsed, the local temperature inside the bubbles is raised very highly (in some cases, to about 5100 K or above, see Suslick et al., *Nature* 434, 52-55) and the pressure increases to 1000 atm or above. Due to such high temperature or pressure, the cellulose sample is disrupted. For details about sonic systems and sonochemistry, please refer, for example, to OHi et al., U.S. Pat. No. 5,766,764, Roberts, U.S. Pat. No. 5,828,156, Mason, Ultrasound: Its Chemical, Physical and Biological Effects, VCH, Weinheim, (1988), Avivi et al., *J. Amer. Chem. Soc.* 121, 4196 (1999) and Avivi et al., *J. Amer. Chem. Soc.* 122, 4331 (2000). For operation of a microcavitation apparatus, please refer to Stuart, U.S. Pat. No. 5,370,999.

An ultrasonic transducer includes a piezoelectric element that converts electrical energy into sonic sound waves.

In case a slurry (e.g. 11-13% (w/v) cellulose sample) is to be sonicated, the transducer may be a commercially available piezoelectric transducer such as Sonics & Materials (USA) Model VCX-600 or 750 (designed to operate at 20 kHz with maximum power of 600 and 750 W, respectively) and Branson Sonics Model 105 or 502 (designed to operate at 20 kHz with maximum power of 3 kW). Also, a high-output sonic transducer is commercially available from, for example, Hielscher Inc. (Ringwood, N.J., USA). This apparatus can deliver a power of 16 kW continuously.

In a specific embodiment of the present disclosure, the sonication is performed by applying sonic waves of 15-130 kHz for 0.5-36 hours to the acid hydrolyzed solid phase. More specifically, sonic waves of 15-80 kHz may be applied for 0.5-30 hours. Most specifically, sonic waves of 15-40 kHz may be applied for 0.5-10 hours.

When sonic waves of 15-130 kHz are applied for 0.5-36 hours, the bonding of cellulose can be disrupted effectively.

The separated solid phase is treated with cellulase to obtain hexose. Through the foregoing physical and chemical pretreatment, the bonding of the ordered cellulose is disrupted and cellulase can easily penetrate through the crevices formed therein. As a result, the efficiency of hydrolysis (saccharification) is improved and a large amount of hexose is obtained.

In a specific embodiment of the present disclosure, the cellulase treatment may be performed at pH 4-7 and 30-70° C. for 24-48 hours. More specifically, the cellulase treatment may be performed at pH 4.8-5 and 48-52° C. for 36-48 hours, slowly at a rate of 100 rpm, according to the cellulase manufacturer's protocol.

In another specific embodiment of the present disclosure, the hexose may be glucose.

And, in a specific embodiment of the present disclosure, the method of the present disclosure further comprises a step of French pressing the sonicated, acid hydrolyzed solid phase following the sonication in the step (d-2). When the biomass is corn stover, sorghum stalk, sugar cane stalk, or wood such as sawdust, it is more desirable to perform French pressing along with the sonication.

As used in the present disclosure, the term "French pressing" has the same meaning as "hydraulic pressing", and the two terms are used interchangeably.

The French pressure cell press (French press) is a hydraulic press using a control valve and a motor-driven pump to vary hydraulic pressure in the press. The press can disrupt bacterial cells under very high mechanical pressure. A cell suspension is supplied into the bore at the center of a steel cylinder cell and pressure is applied to the sample. As the pressure in the French pressure cell increases, the pressure inside the cells is also increased. When the pressure reaches 32,000-35,000 psi, the sample is distributed through the sample injection tube by means of the small Teflon ball attached to the screw valve. This allows the pressure outside the cell wall to rapidly decrease down to the atmospheric pressure. The pressure in the cells also decreases, but not so fast as the pressure outside the cells. Due to the pressure difference, the cell wall is disrupted immediately and, consequently, cellulose and hemicellulose are also disintegrated. A continuous fill protocol is useful when disrupting a large volume of cells (>100 mL).

In a more specific embodiment of the present disclosure, the French pressing may be performed at a pressure of 25,000-40,000 psi, more specifically 30,000-40,000 psi, most specifically 31,000-36,000 psi.

When the French pressing is performed at a pressure of 25,000-40,000 psi, the cell wall is disrupted due to pressure difference and, as a consequence, cellulose and hemicellulose are disrupted.

(e) Fermentation of Pentose, Hexose, or Pentose and Hexose by Treating with Ethanol-Producing Fermenting Microorganism The pentose, hexose, or pentose and hexose obtained through the physical and chemical pretreatment is fermented treating with ethanol-producing fermenting microorganism to obtain ethanol, the final product.

The ethanol-producing fermenting microorganism used in the present disclosure may include various microorganisms known in the art that produce ethanol as fermentation product. Specifically, the microorganism may be yeast. More specifically, the yeast may belong to the genus *Saccharomyces, Schizosaccharomyces, Sporobolomyces, Torulopsis, Trichosporon, Wickerhamia, Ashbya, Blastomyces, Candida, Citeromyces, Crebrothecium, Cryptococcus, Debaryomyces, Endomycopsis, Geotrichum, Hansenula, Kloeckera, Lipomyces, Pichia, Rhodosporidium* or *Rhodotorula*. More specifically, it may be yeast belonging to the genus *Saccharomyces*. Most specifically, it may be *Saccharomyces cerevisiae, Saccharomyces baynus* or *Saccharomyces carlsbergensis*.

Figure 1:
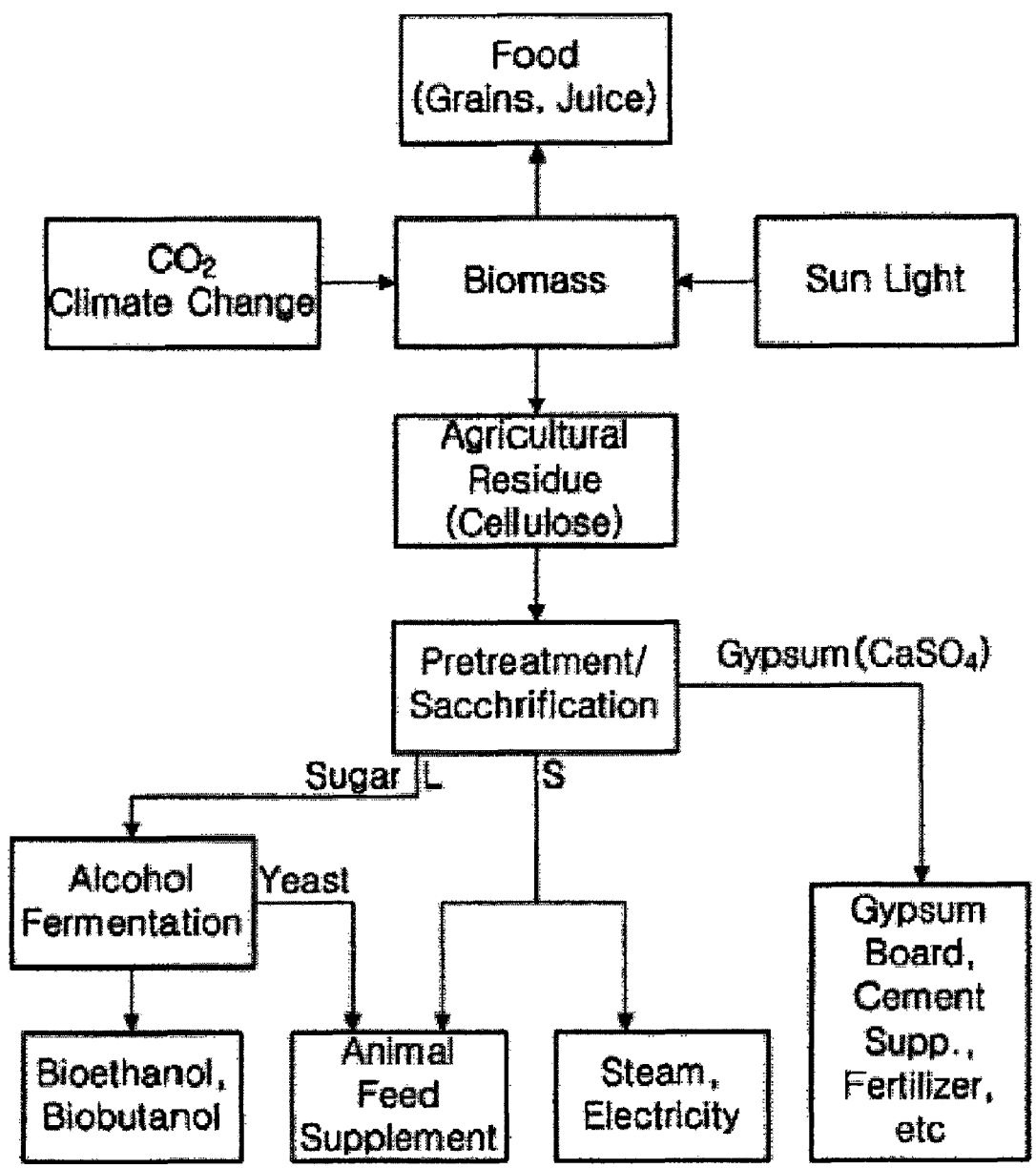
FIG. 1 is a block diagram illustrating production of bioenergy using non-food biomass and utilization of by-products.

The examples and experiments will now be described. The following examples and experiments are for illustrative purposes only and not intended to limit the scope of this disclosure.

EXAMPLES

Materials and Methods

Strain and Culture Condition

Standard yeast (*Saccharomyces cerevisiae*; Strain No. 7905) acquired from the Microbial Resource Center of the Korea Research Institute of Bioscience & Biotechnology (KRIBB) was used. The yeast was cultured in a shaking incubator at 30° C. using YM medium (yeast extract 3 g, malt extract 3 g, peptone 5 g, dextrose 10 g, distilled water 1 L, pH 6.3).

Ethanol fermentation was performed as follows using glucose obtained from disintegration of cellulose. The yeast that had been preserved in slant medium was inoculated in 100 mL of YM broth and incubated at 30° C. for 24 hours with shaking. The yeast was recovered by centrifugation, washed with saline, and then resuspended in 5 mL of dextrose-free YM medium. All the suspended yeast was inoculated in 200 mL of glucose-containing cellulose hydrolysate that had been passed through 0.2 μm filter, and fermented under microaerobic condition at 30° C. for 24 hours or 48 hours. Then, the amount of produced ethanol was quantitated by HPLC (Waters 2690, USA).

Pulverization, Acid Treatment and Preparation of Slurry

Dried rice straw, fruit skin or corn stover was pulverized using a Shinil mixer (SMX-3000JS) for 5-6 cycles with ON for 30 seconds and OFF for 3 minutes, passed through a sieve with an average mesh size of 1 mm, and dried at 95° C. for 3 hours to prepare a sample for acid treatment. Acid hydrolysis treatment was performed using a Hirayama high-pressure autoclave (HVA-110) at 130° C. for 40 minutes after adding 50-100 g of the pulverized sample in a 2 L beaker and suspending well after adding about 500-1000 mL of diluted sulfuric acid (0.5-2%). The acid hydrolyzed sample was cooled and passed through Advantec filter paper (#2, 150 mm) to separate the liquid phase that passes through the filter from the solid phase that does not. The separated liquid phase was neutralized with $CaCO_3$ and xylose content was measured by HPLC (Waters 2690, USA). And, the solid phase was pulverized using a Brown home mixer for 10 minutes for 2 cycles with ON for 30 seconds and OFF for 1 minute, and prepared into a slurry (dry solid content: 11-13% (w/v)) for physical pretreatment such as sonication and French pressing.

Sonication

High-intensity sonic processors (VCX-600 and VCX-750, Sonics & Materials (USA)) was used as sonicator. A 3 mm tapered microtip and a 13 mm standard tip were used.

Sonication was performed as follows.

A small-volume (30 mL) slurry was put in a 50 mL centrifuge tube (Corning) and treated on ice for 4 minutes, for 5-10 times. A large-volume (1 L) slurry was put in a 1 L beaker and sonicated for 5-24 hours using a pulser (ON for 9 seconds, OFF for 9 seconds) with amplitude 15% or less, while stirring the slurry at 100 rpm using an IKA mixer (RW 20 DZM.n). When a 13 mm standard tip was used, sonication was performed for 1-5 hours with ON for 10 seconds and OFF for 20 seconds.

French Pressing

French pressing was performed using SLM-Aminco's French® Pressure Cell Press. A 40 K French pressure cell was used. 25 mL of the sonicated sample was put in the cell and treated 3-6 times at a pressure of 32,000-35,000 psi. If necessary, sonication was performed again to make hydrolysis by cellulase easier.

Cellulase for Saccharification

Cellulase was purchased from Novozymes (Bagsvard, Denmark). Celluclast® 1.5 L and 10,000 NCU (1,500 NCU/g) of Novozyme®188 330 Cbu (250 Cbu/g) were added to 1 kg of the slurry that had been sonicated alone or sonicated and French pressed. After slowly stirring at 100 rpm, at pH 4.8 and 50° C., for 24, 30, 36, 42 or 48 hours, the degree of hydrolysis was compared. The enzyme-treated sample was rotated at 8,000 rpm for 15 minutes using a Hanil high-speed centrifuge (Supra 22K) and a Hanil A2505-6N rotor and then separated into solid and liquid phases. The glucose-containing liquid phase was filtered using a 142-mm pressure filtration holder equipped with a filter of 0.2 μm pores, and sealed and kept in a refrigerator after measuring the glucose concentration using the Sigma glucose assay kit GAHK-20 (Sigma-Aldrich, USA).

HPLC Analysis and Measurement of Glucose Concentration

Ethanol, furfural and xylose were quantified by HPLC (Waters 2690, USA) at 65° C. with flowing 5 mmol sulfuric acid at 0.5 mL/min, using an Aminex HPX-87-H column (300 mm×7.8 mm, Bio-Rad, USA) and an RI detector. All the samples to be analyzed had been passed through an HPLC membrane filter with a pore size of 0.2 μm. Glucose content was measured using the Sigma glucose assay kit GAHK-20 (Sigma-Aldrich, USA) according to the manufacturer's protocol.

Result and Discussion

Overall Concept

FIG. 1 is a block diagram illustrating production of bioenergy using non-food biomass and utilization of by-products.

As a result of photosynthesis, carbon dioxide in the atmosphere, which is the cause of global climate change, is converted into biomass. After food resources such as corn kernel, rice, wheat, fruit juice, sugar cane, etc. are removed, the remaining non-food resources such as corn stover, rice straw, wheat straw, fruit skin, sugar cane bagasse, etc. are converted in large scale into renewable energy such as bioethanol or biobutanol. The by-products can be used as livestock feed additives, fuels for steam and power generation, raw materials of gypsum board, cement additives, fertilizers, or the like.

Overall Process

Figure 2:
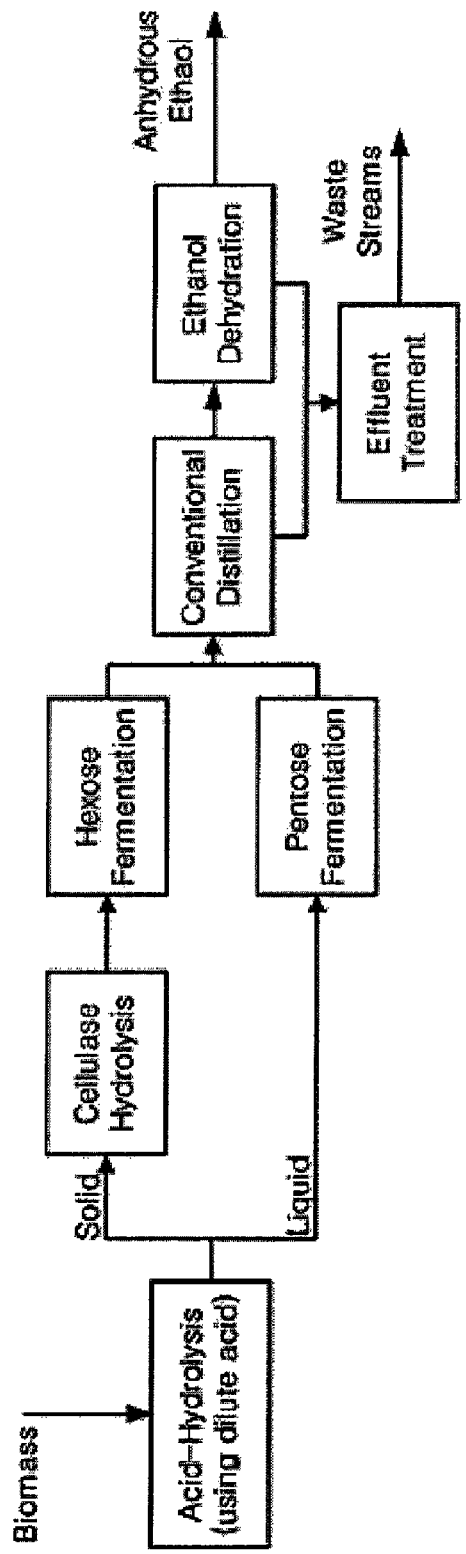
FIG. 2 is a block diagram illustrating conversion of biomass into ethanol via continuous treatment of feedstock.
Figure 3:
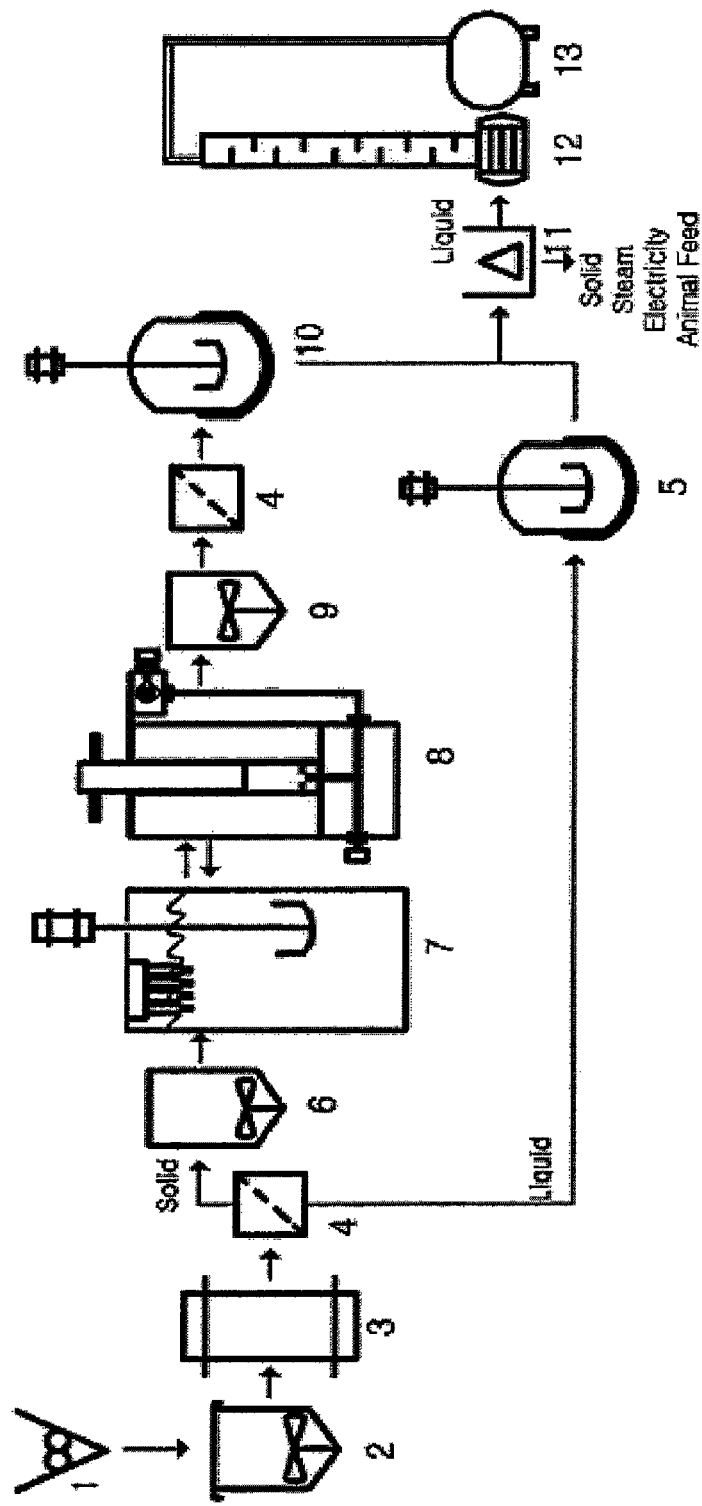
FIG. 3 is a schematic diagram illustrating a process of converting cellulose into a product (e.g., ethanol) (1: mill; 2: knife cutter; 3: acid hydrolysis chamber; 4: solid-liquid separation filter; 5: pentose fermentation reactor; 6: knife cutter; 7: sonication chamber; 8: hydraulic press (French press); 9: cellulose saccharification chamber; 10: hexose fermentation reactor; 11: centrifuge; 12: distillation column; 13: ethanol storage tank).
Figure 4:
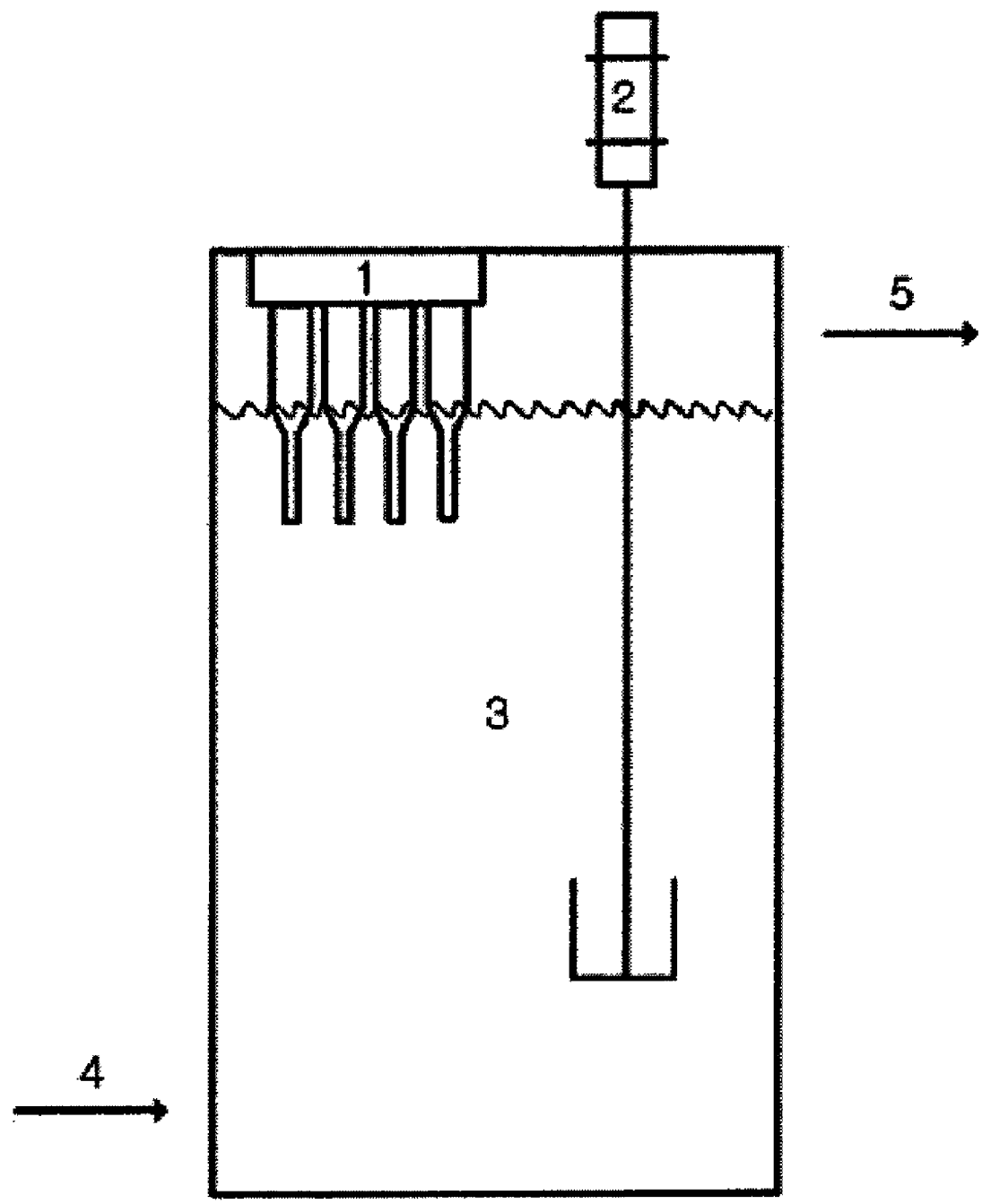
FIG. 4 is a cross-sectional view of a sonication chamber (1: multi-element sonicating probes; 2: mixer; 3: sonication chamber; 4: inlet; 5: outlet).
Figure 5:
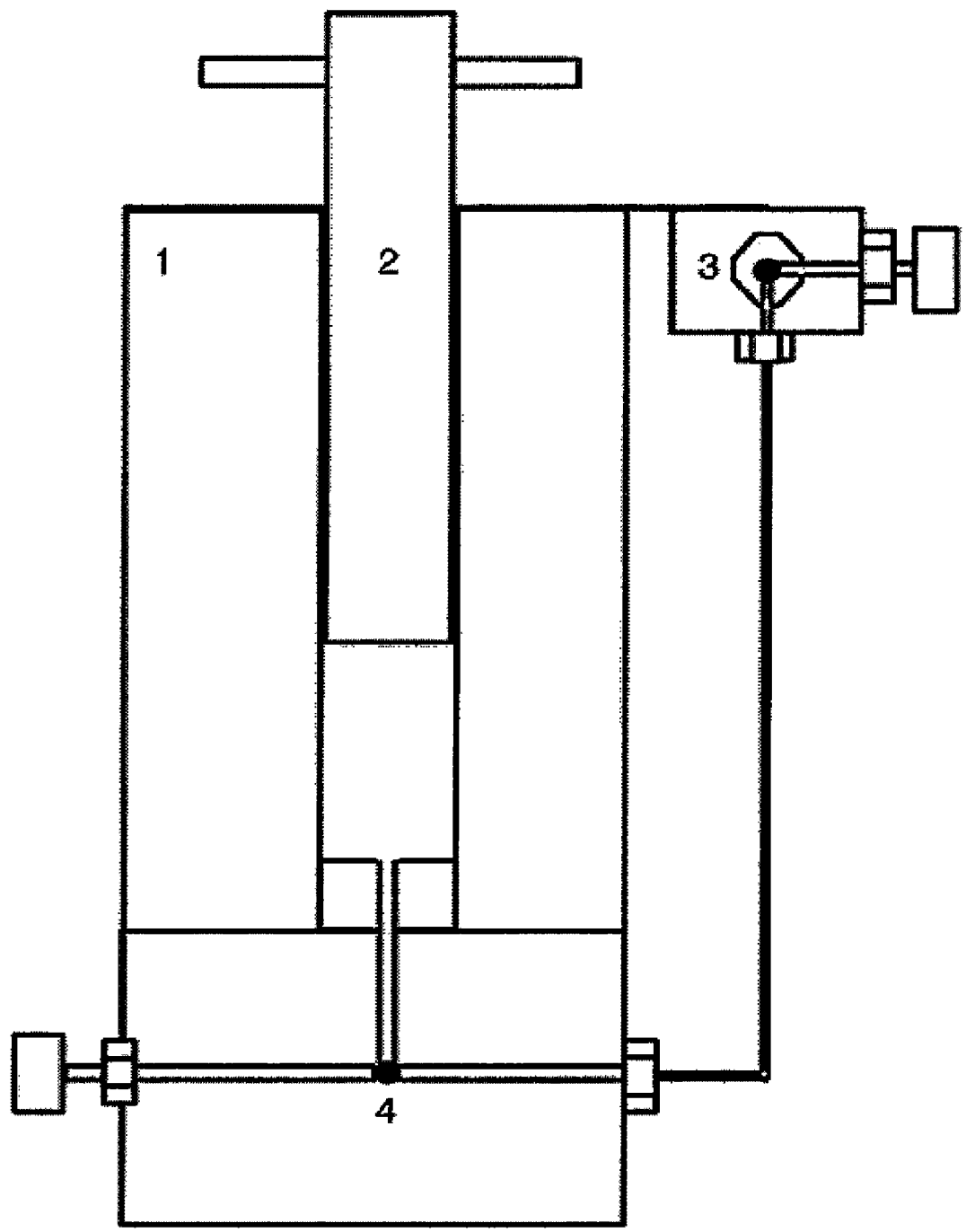
FIG. 5 is a cross-sectional view of a French pressure cell (40 K, SLM-Aminco, USA) (1: French pressure cell (40 K); 2: piston; 3: inlet; 4: outlet).

FIG. 2 is a block diagram illustrating conversion of biomass into ethanol via continuous treatment of feedstock.

The production of ethanol from lignocellulosic biomass comprises the following five steps: 1) pretreatment of biomass, 2) hydrolysis of cellulose, 3) fermentation of hexose and pentose, 4) conventional distillation and ethanol dehydration, and 5) effluent treatment.

It is to be noted that the method of the present disclosure does not require detoxification, sulfuric acid reconcentration and delignification processes.

The figure shows that the solid phase of a pretreated lignocellulose sample is hydrolyzed (saccharified), and the solid phase contains cellulose that can be treated by cellulase. After hydrolysis by cellulase, the resultant cellulose hydrolysate is fermented and converted into ethanol. The fermentation of hexose and pentose is performed in separate units.

Pulverization and Acid Hydrolysis

Figure 6:
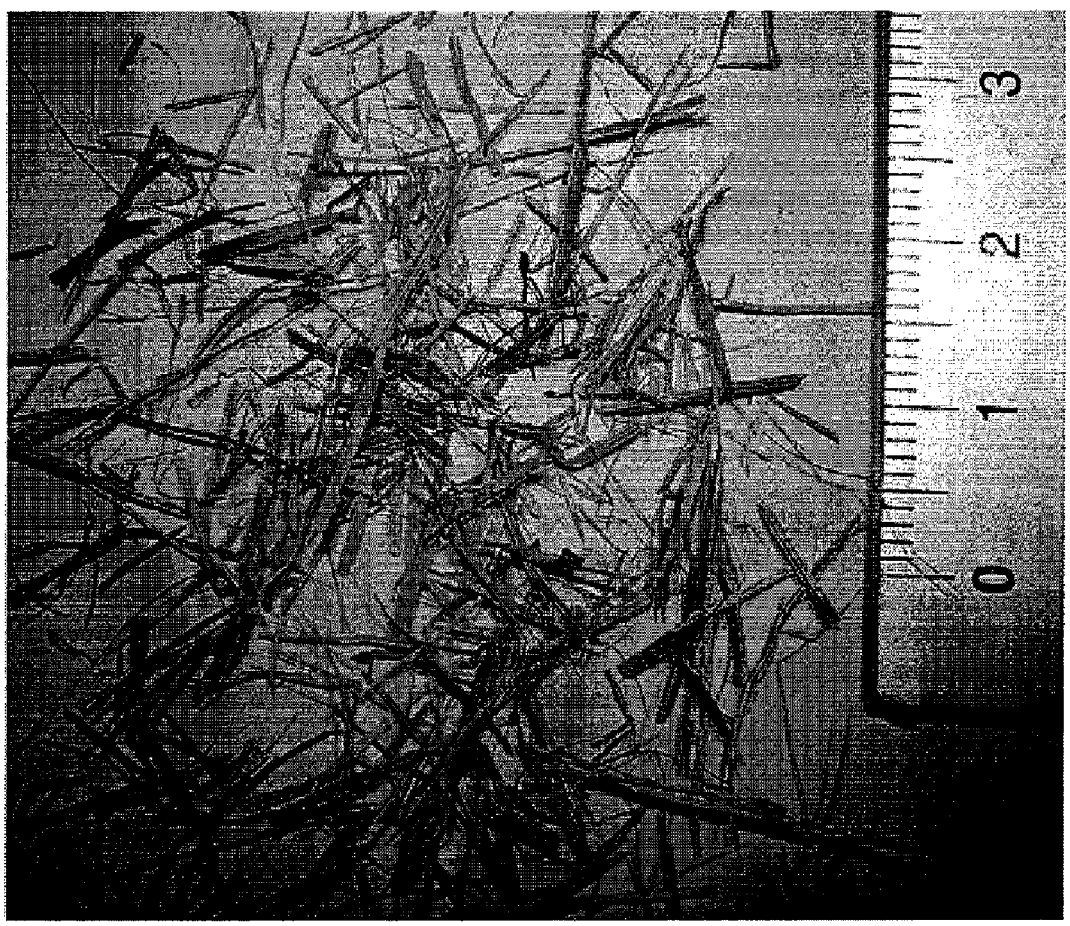
FIG. 6 shows fibrous materials produced from rice straw by a mill. The scale is in cm unit.
Figure 7:
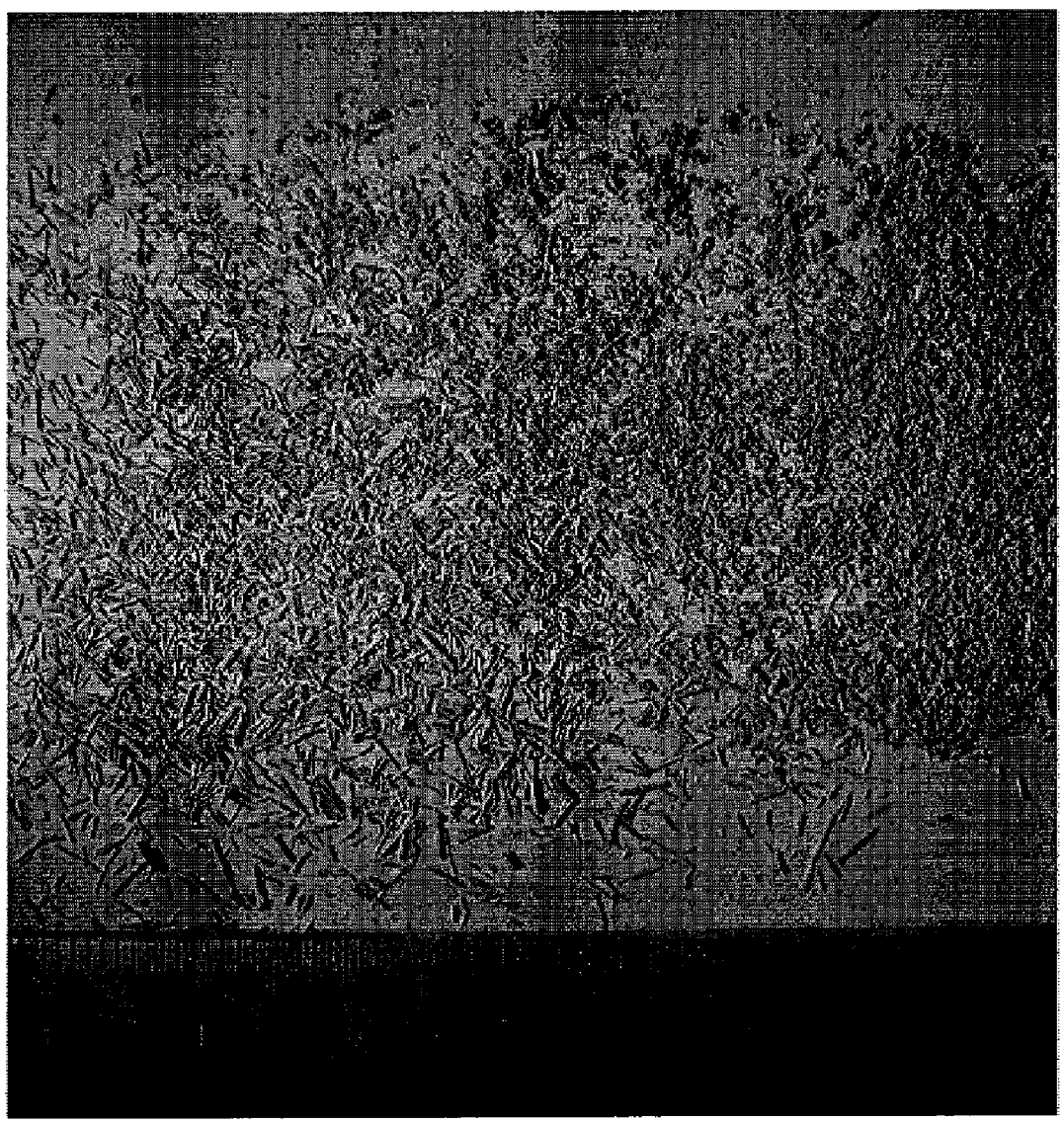
FIG. 7 shows fibrous materials pulverized by a knife cutter and passing through 1 mm meshes before acid hydrolysis pretreatment. The scale is in cm unit.
Figure 8:
FIG. 8 is a 100× microscopic image of fibrous materials pretreated by acid hydrolysis.
Figure 9:
FIG. 9 is a 100× microscopic image of fibrous materials produced from rice straw. The fibrous materials were obtained by pulverizing a solid phase separated after acid hydrolysis pretreatment at least once using a knife cutter.

Dried rice straw consists of cellulose (36%), hemicellulose (26%), lignin (20%), crude protein (5%) and ashes (13%). In Korea, about 500 kg is produced per 10 a. The rice straw was cut to a size of the sample as shown in FIG. 6, further pulverized using a Shinil home mixer, and passed through 1 mm meshes to prepare the sample for acid hydrolysis as shown in FIG. 7. For acid hydrolysis, the sample was suspended in 2% sulfuric acid and, after treating at 130° C. for 40 minutes (FIG. 8), and the solid phase was separated by filtering and further pulverized for 10 minutes using a Brown home mixer (FIG. 9). A 100× optical microscopic image of the sample (FIG. 9) reveals that the sample was pulverized to smaller size than that after the acid hydrolysis (FIG. 8). Since the sample had been softened by the acid hydrolysis treatment, it could be pulverized easily (in short time) with small force (small-sized motor) and energy consumption could be saved. The average size of the pulverized solid phase was about 0.25 mm or smaller.

Fruit skin (orange peel) was dried indoors, pulverized using a Shinil home mixer, passed through 1 mm meshes, suspended in 1.5% sulfuric acid, and treated at 130° C. for 40 minutes. The following process was the same as that for the rice straw.

Figure 15:
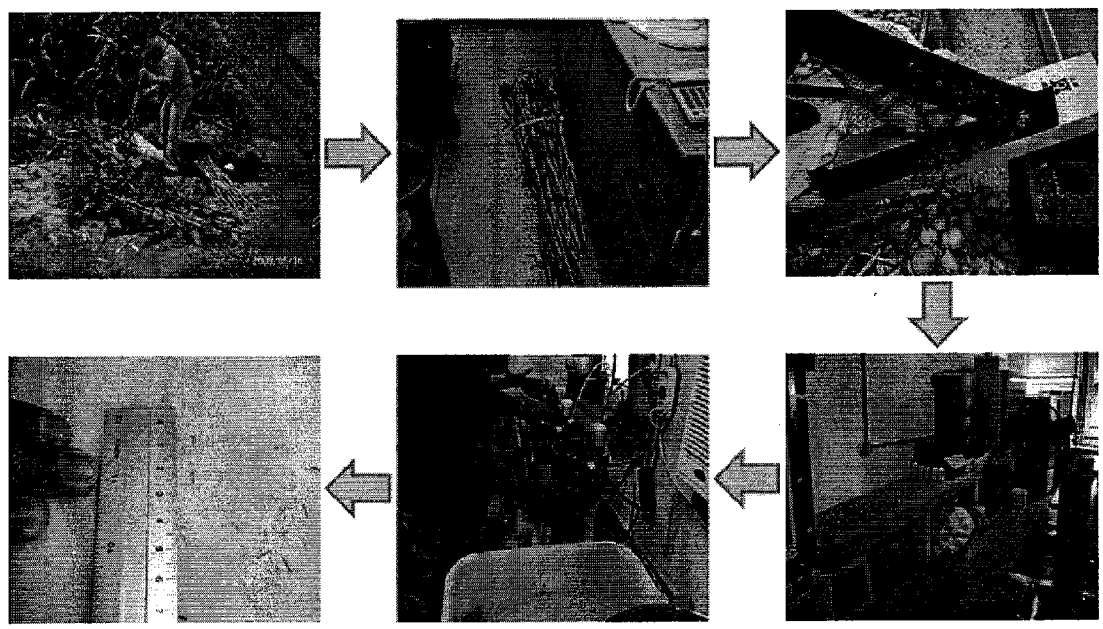
FIG. 15 shows pulverization of corn stover for pretreatment. Corn stover is cut to a length of about 5 mm using a straw cutter, which is then dried and pulverized in a pulverizer for 5-6 cycles with ON for 30 seconds and OFF for 3 minutes.

Corn stover was chopped to a length of about 5 mm using a straw cutter, dried indoors, and pulverized for 5-6 cycles with ON for 30 seconds and OFF for 3 minutes using the same mixer (FIG. 15). The pulverized corn stover sample was suspended in 1.5% sulfuric acid and treated at 130° C. for 40 minutes. The following process was the same as that for the rice straw.

Sonication and French Pressing

Figure 10:
FIG. 10 is a 100× microscopic image of fibrous materials produced from rice straw, after sonication.
Figure 11:
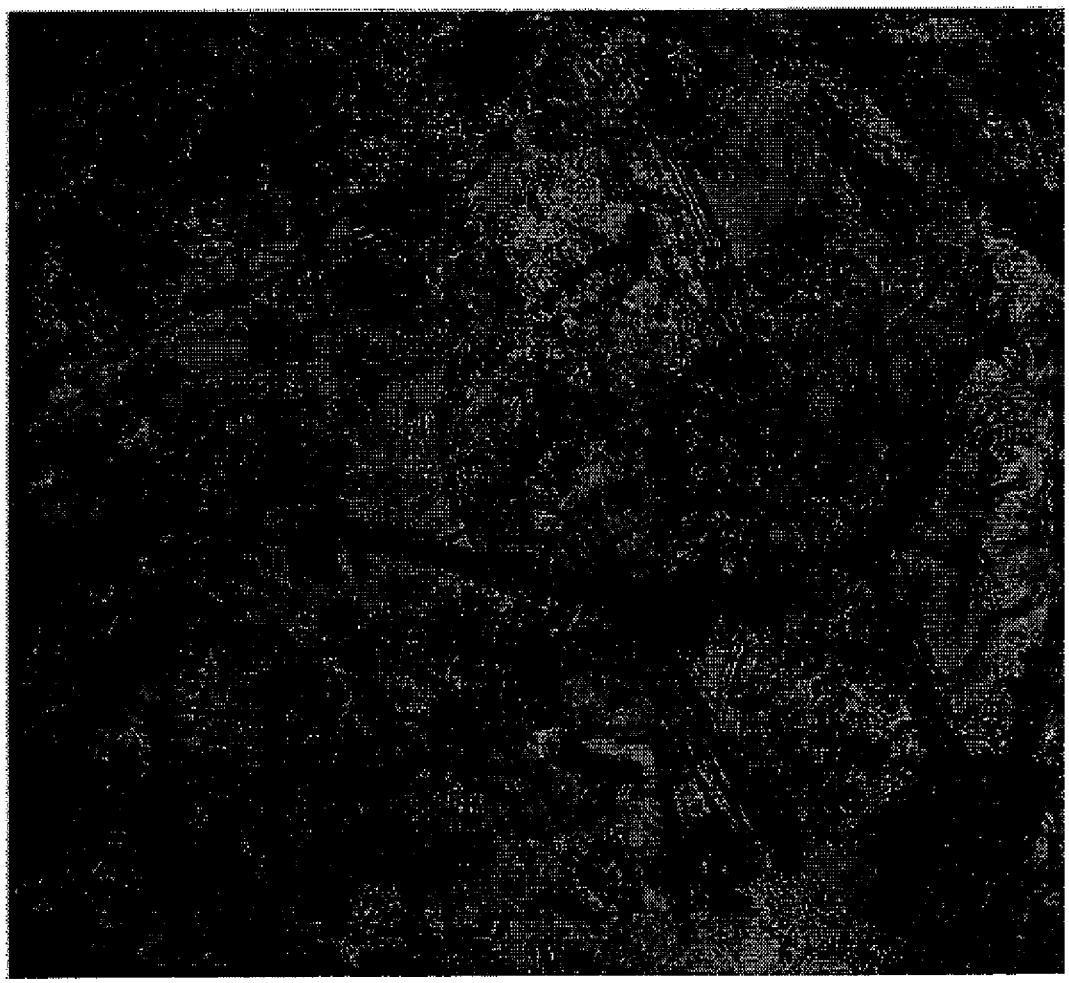
FIG. 11 is a 100× microscopic image of fibrous materials produced from rice straw, after sonication and French pressing. The regularly aligned cellulosic fibrils are disrupted, thus allowing easy access of cellulase.
Figure 16:
FIG. 16 is a 100× microscopic image of a sample treated with 1.5% sulfuric acid at 130° C. for 40 minutes (left), and further treated by sonication and French pressing (right). The addition of the physical treatment resulted in a random, disrupted structure, which allows easy penetration of enzyme through the crevices formed therein for easier saccharification.
Figure 16:
Figure 16:
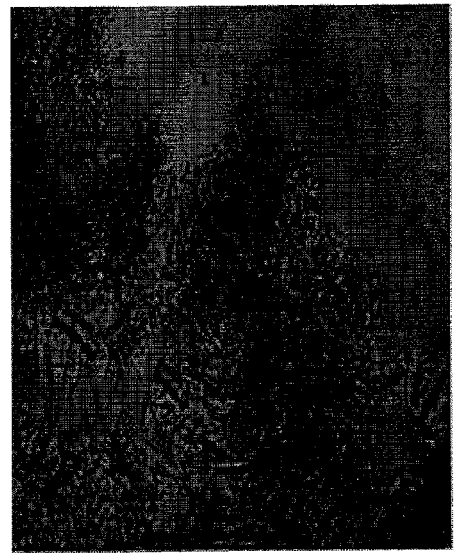
Figure 17:
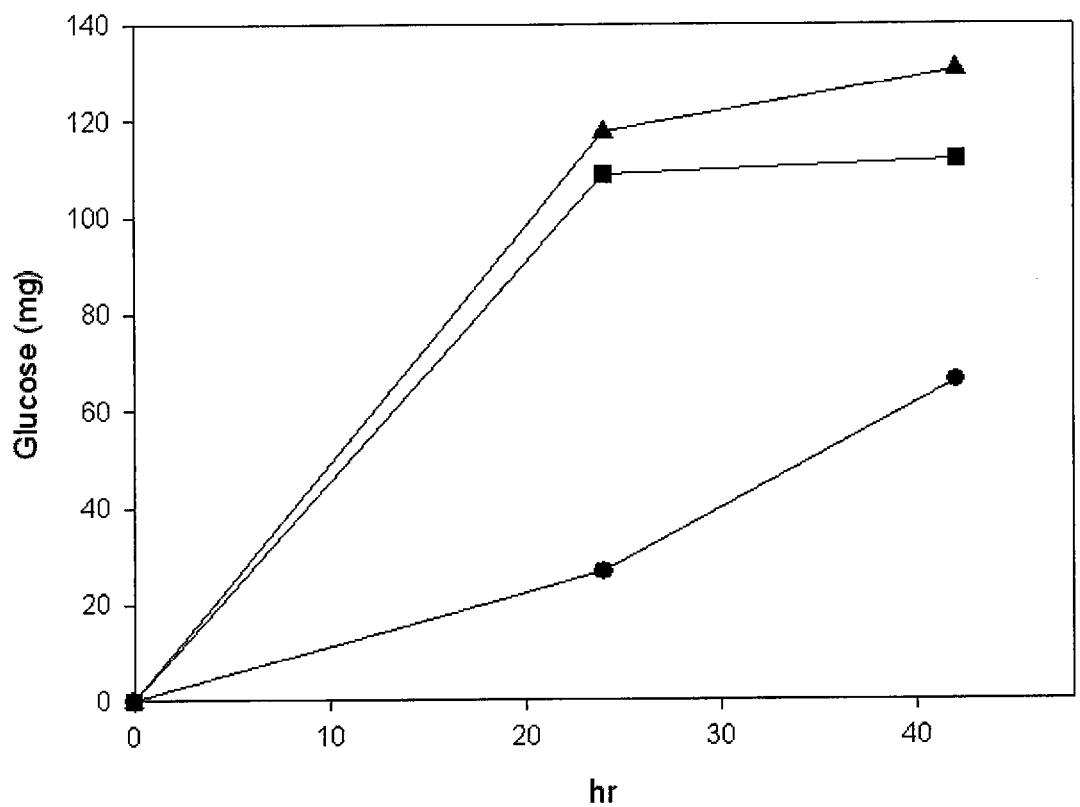
FIG. 17 shows the effect of each physical treatment on the saccharification of corn stover (●: amount of glucose produced without treatment; ■: amount of glucose produced after sonication; ▲: amount of glucose produced after sonication and French pressing).

FIG. 10 shows the sonicated rice straw sample, FIG. 11 shows the sonicated and French-pressed rice straw sample, and FIG. 16 shows the corn stover sample before and after sonication and French pressing. It can be seen that, after the sonication, the rice straw cells were disrupted and cellulose was disintegrated. After the French pressing, the sample was further disintegrated. When the sonication time was increased, a result similar to that of FIG. 11 could be attained even without French pressing, and sufficient saccharification could be achieved by cellulase. Accordingly, it can be seen that the French pressing is not absolutely necessary for rice straw. In case of sawdust, the disruption of cellulose was appreciably increased by French pressing. As for corn stover, the French pressing treatment increased the saccharification efficiency (42 hours) by 17% (FIG. 17). The celluloses that had been regularly arranged in crystal form were disrupted and disintegrated by the acid hydrolysis, sonication and pressing treatments. It is though that cellulase can easily penetrate through the crevices formed therein and thus increases the hydrolysis (saccharification) efficiency.

Combination of Physical and Chemical Treatments

Figure 12:
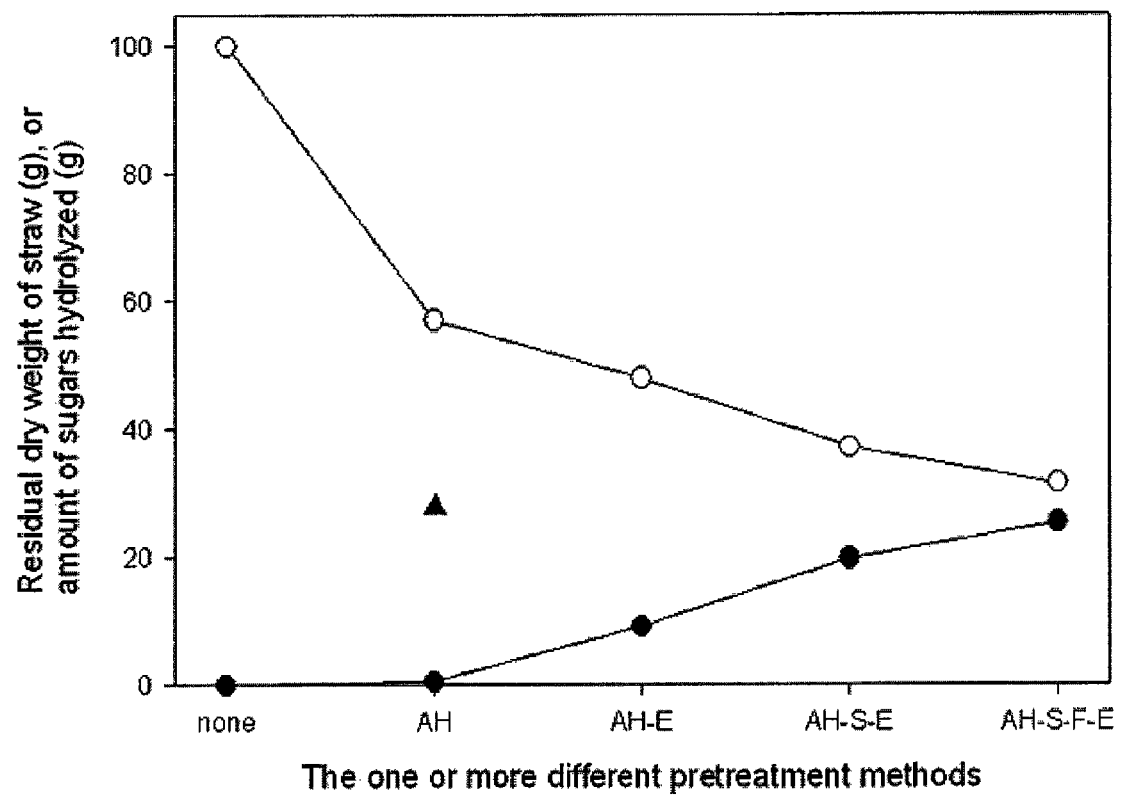
FIG. 12 shows the effect of one or more different pretreatment methods on the hydrolysis of rice straw (none: non-treated; AH: acid hydrolyzed; S: sonicated; F: French pressed; E: cellulase-treated. ○: residual dry weight (g) of rice straw; ●: amount (g) of hydrolyzed glucose; ▲: amount (g) of xylose produced by acid hydrolysis).

FIG. 12 shows the effect of combination of the physical and chemical pretreatment methods on the hydrolysis of and glucose production from rice straw. 100 g of rice straw samples dried at 95° C. for 3 hours were used for comparison.

After acid hydrolysis at 130° C. for 40 minutes using 2% sulfuric acid (AH in FIG. 12), the dry residue weight was 56.7 g, and the amount of produced pentose (xylose) and hexose (glucose) was 27.9 g and 0.51 g, respectively. The reason why such a large amount of xylose was obtained is because most of hemicellulose, which comprises mainly the xylose, was easily hydrolyzed under the condition (Karin Ohgren et al., High temperature enzymatic prehydrolysis prior to simultaneous saccharification and fermentation of steam pretreated corn stover for ethanol production. *Enzyme and Microbial Technology* 40: 607-613 (2007)).

It was reported that, when the wheat bran sample was treated with 2% sulfuric acid, furfural, which is the representative inhibitor of fermentation, was produced as much as 0.4 g/L up to 130° C., and increased abruptly from 140° C. to a level of inhibiting fermentation (4 g/L) at around 150° C. (Beatriz Palmarola-Adrados et al., Ethanol production from non-starch carbohydrates of wheat bran. *Bioresource Technology* 96: 843-850 (2005)).

Under the condition described in the example of the present disclosure, 0.18 g/L of furfural was detected and ethanol fermentation was achieved easily. Thus, it can be seen that such a concentration of furfural is not so high as to affect the fermentation. Accordingly, the method of the present disclosure, wherein diluted sulfuric acid is used, is an economical and simple pretreatment process not requiring detoxification, sulfuric acid reconcentration, recycling and delignification processes.

Cellulase was added to the residue remaining after the acid hydrolysis and made to react at 50° C. for 42 hours as described in Materials and Methods (AH-E in FIG. 12). The amount of the residue remaining after the acid hydrolysis was 47.9 g and the amount of produced glucose was 9.1 g, strongly indicating that most of cellulose remains unhydrolyzed by the cellulase and further pretreatment is necessary.

Because of such inefficiency of saccharification, pretreatment was not an easy process. It is reported that 20-49% of glucose yield was obtained by a costly multi-step pretreatment method including steam explosion followed by treatment with four enzymes-xylanase, ferulic acid esterase, cellulase and laccase (M. G. Tabka et al., Enzymatic saccharification of wheat straw for bioethanol production by a combined cellulase xylanase and feruloyl esterase treatment. *Enzyme and Microbial Technology* 39: 897-902 (2006)).

Also, there is the total acid hydrolysis of treating with strong 72% sulfuric acid. However, this use of the strong sulfuric acid causes corrosion of apparatus and reconcentration of the used, diluted sulfuric acid is necessary. In addition, a detoxification process is needed to remove toxic substances and a lot of waste is generated.

The method according to the present disclosure is of high economic value since it does not need such additional processes and waste generation is minimized.

After the acid hydrolysis, the resulting solid slurry was further sonicated and made to react at 50° C. for 42 hours after adding cellulase, as described in Materials and Methods (AH-S-E in FIG. 12). Also, after the sonication, French pressing was performed followed by the addition of cellulase and reaction as described above (AH-S-F-E in FIG. 12). The dry weight of the residue was 37.2 g and 31.6 g, respectively, and the amount of produced glucose was 19.8 g and 25.4 g, respectively.

Since cellulose is included in rice straw in an amount of about 36%, the fact that 25.4 g of glucose was produced indicates that 70% or more of cellulose was hydrolyzed and converted into glucose. When summed with the amount of xylose (28 g), it means that 53.4 g of sugar was obtained from 100 g of rice straw.

The corn stover slurry hydrolysate was prepared in the same manner as for the rice straw, except that it was treated with 1.5% sulfuric acid at 130° C. for 40 minutes. The effect of various combinations of physical treatment on the saccharification of the corn stover slurry is as follows. For non-treatment, sonication and sonication as well as French pressing, the amount of glucose produced 24 hours after the addition of enzyme was 26.7, 108.8 and 117.6 mg, respectively. 42 hours later, it was 66.0, 111.8 and 130.4 mg, respectively (FIG. 17). In particular, glucose was produced 4.1-4.4 times faster until 24 hours, and the production rate was the fastest when French pressing was carried out. Cellulose-to-glucose conversion ratio was 71% upon sonication, and very high as 83% upon sonication as well as French pressing.

This result demonstrates that the saccharification pretreatment process according to the present disclosure is very effective in producing sugar.

When the sawdust sample was acid hydrolyzed, sonicated and French-pressed in the same manner as that for rice straw, the glucose yield was about ½ that of rice straw. This may be due to the fact that wood is stronger than rice straw because of the presence of lignin and thus is less disrupted by sonication and French pressing. However, considering that the output of the sonicator used in the example of the present disclosure was 600 W, a better glucose yield might be achieved using a commercialized sonicator with an output of 3 kW or 16 kW. And, when a stronger sonicator is used, a higher yield may be obtained.

Effect of Reaction Time

Figure 13:
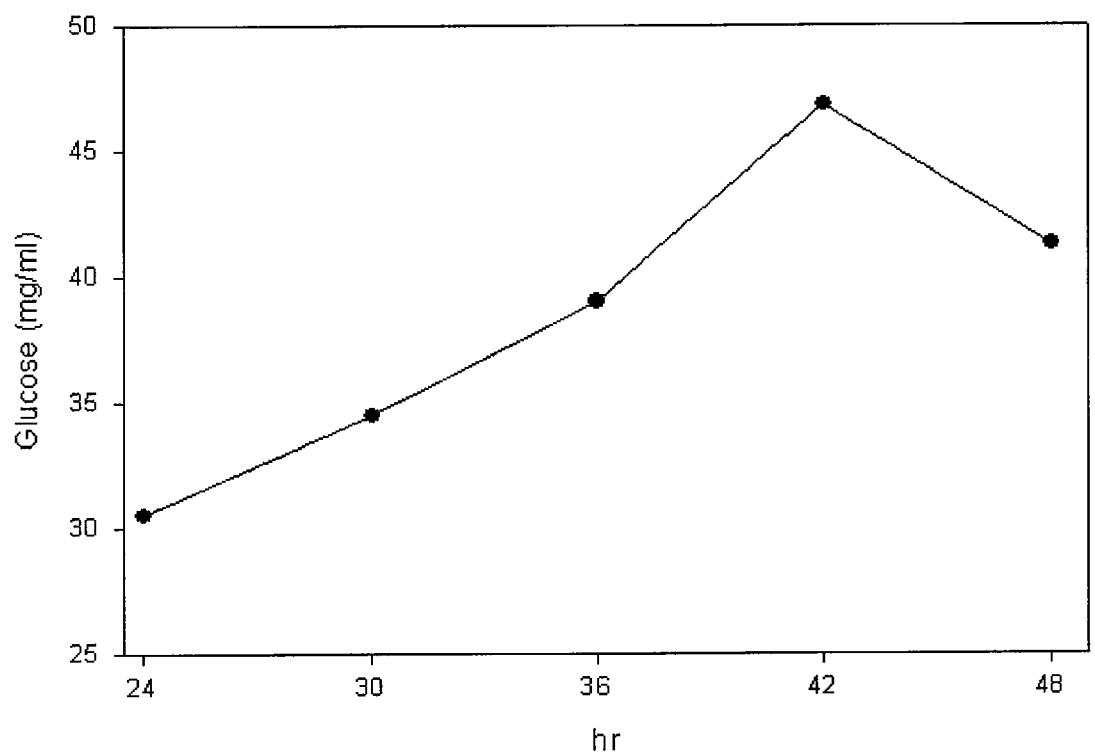
FIG. 13 shows the amount of glucose produced by cellulase from a sonicated rice straw sample. A predetermined amount of cellulase was added to sonicated rice straw and the concentration of glucose was measured as described in Materials and Methods.

After adding cellulase to rice straw slurry as described in Materials and Methods, glucose concentration was measured after 24, 30, 36, 42 and 48 hours of reaction at pH 4.8 and 50° C. (FIG. 13). The glucose concentration was highest at 46.8 mg/mL when the reaction was performed for 42 hours. Also with the corn stover, the glucose concentration was highest (37.3 mg/mL) when the reaction was performed for 42 hours. It was recently reported that 22-23 mg/mL of glucose was obtained from corn stover and rice straw by steam explosion (Symposium—Biofuel industry using wood-derived biomass and pretreatment process, The 6th Green Energy Expo Korea, Korea Forest Service, Apr. 8, 2009, EXCO, Daegu). The method according to the present disclosure provides 2 times higher glucose concentration than the reported result. Thus, it can be seen that the method of the present disclosure is a very effective biomass pretreatment method.

Production of Bioethanol

Figure 14:
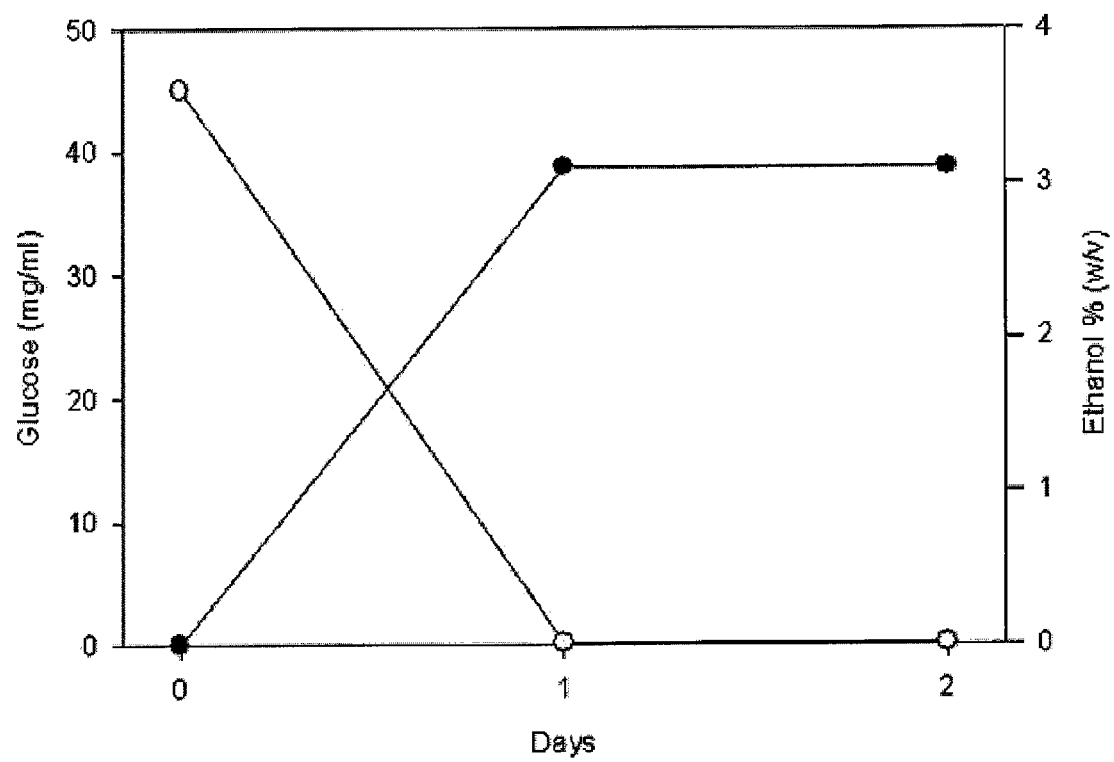
FIG. 14 shows the concentration of glucose and ethanol in a rice straw hydrolysate with fermentation time (○: glucose concentration; ●: ethanol concentration).
Figure 18:
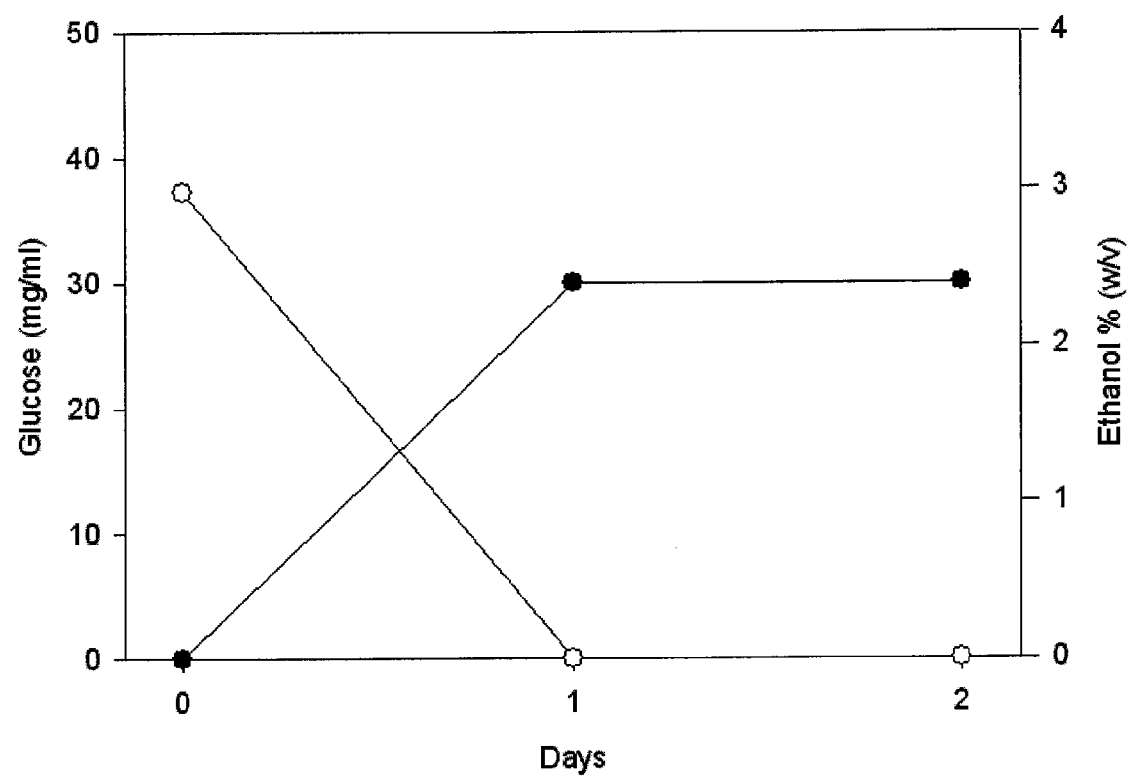
FIG. 18 shows the concentration of glucose and ethanol in a corn stover hydrolysate with fermentation time (○: glucose concentration; ●: ethanol concentration).
Figure 19:
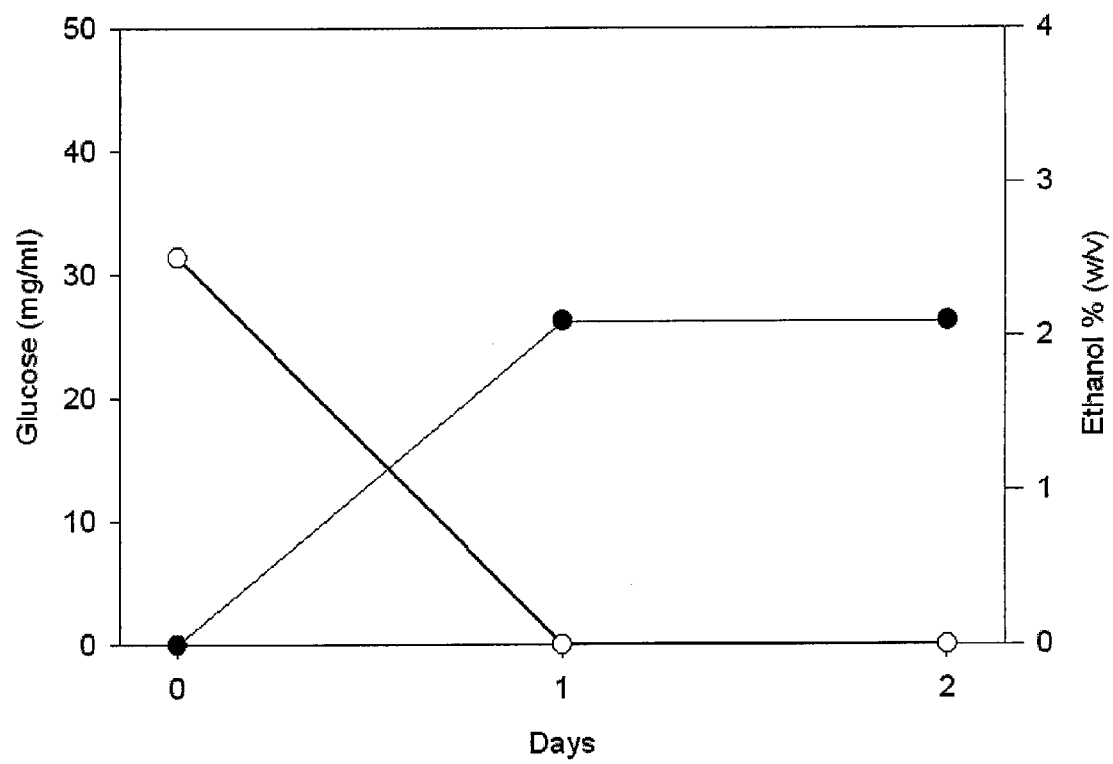
FIG. 19 shows the concentration of glucose and ethanol in an orange peel hydrolysate with fermentation time (○: glucose concentration; ●: ethanol concentration).

Rice straw (FIG. 14), corn stover (FIG. 18) and orange peel (FIG. 19) were sonicated as described in Materials and Methods, and the resultant hydrolysate was subjected to ethanol fermentation. On the next day of inoculation, almost all the glucose in the medium was consumed, and 3.1% (FIG. 14), 2.4% (FIG. 18) and 2.1% (FIG. 19) of ethanol was produced, respectively. This result suggests that the substance that inhibits fermentation was not produced during the pretreatment and that the sugar obtained from the saccharification is a good substrate for ethanol fermentation.

As described in detail above, the present disclosure provides a method for preparing bioethanol from biomass. According to the present disclosure, the feedstock for preparation of bioethanol, i.e. the biomass, is pretreated by a combination of chemical and physical methods. The method is advantageous in that detoxification is unnecessary since the substances that inhibit fermentation are not produced and acid reconcentration for recycling is not needed. Further, since the sonication makes saccharification easier, removal of lignin (delignification), which interferes with the saccharification of cellulose, is unnecessary. Accordingly, the present disclosure allows to produce bioethanol with high yield and at low cost in an environment-friendly manner.

The present disclosure presents a method for producing new renewable energy allowing to cope with the global climate change by removing carbon dioxide from the atmosphere by photosynthesis, without affecting the global grain prices. And, the by-product produced during bioethanol production may be used as livestock feed additives, fuels for steam and power generation, raw materials of gypsum board, cement additives, fertilizers, or the like. Thus, the present disclosure provides a method for utilizing non-food biomass from corn stover, rice straw, wheat straw, fruit skin, sugar cane stalk or sorghum stalk, which are available in large scale at low cost, 100% as a valuable resource.

While the present disclosure has been described with respect to the specific embodiments, it will be apparent to those skilled in the art that various changes and modifications may be made without departing from the spirit and scope of the disclosure as defined in the following claims.

What is claimed is:

1. A method for preparing ethanol from biomass, comprising the steps of:
   (a) pulverizing biomass;
   (b) hydrolyzing the pulverized biomass by treating with sulfuric acid;
   (c) separating the resultant of the step (b) into liquid and solid phases;
   (d) (d-1) neutralizing the liquid phase of the resultant of the step (c) by treating with calcium carbonate ($CaCO_3$) as a neutralizer to obtain pentose and to form $CaSO_4$, and, (d-2) sonicating the solid phase of the resultant of the step (c) and treating the same with cellulase to obtain hexose; and
   (e) fermenting the pentose and hexose of the step (d-1) and (d-2) by treating with ethanol-producing fermenting microorganism.

2. The method according to claim 1, wherein the biomass is selected from a group consisting of rice straw, wheat straw, corn cob, corn stover, rice husk, paper, wood, sawdust, agricultural waste, grass, sugar cane bagasse, cotton, flax, bamboo, abaca, algae, fruit skin and seaweed.

3. The method according to claim 1, which further comprises, between the step (a) and the step (b), a step of (a-1) passing biomass pulverized in the step (a) through meshes with one side being 0.25-5 mm in length.

4. The method according to claim 1, wherein the hydrolysis in the step (b) is performed with a 0.1-10% (v/v) acid at 100-150° C. for 20-60 minutes.

5. The method according to claim 1, wherein the sonication in the step (d-2) is performed by applying sonic waves of 15-130 kHz for 0.5-36 hours to the acid hydrolyzed solid phase in the step (c).

6. The method according to claim 1, which further comprises French pressing after the sonication in the step (d-2).

7. The method according to claim 6, wherein the French pressing is performed at 25,000-40,000 psi.

8. The method according to claim 1, wherein the cellulase treatment in the step (d-2) is performed at pH 4-7 and 30-70° C. for 24-48 hours.

9. The method according to claim 1, wherein the ethanol-producing fermenting microorganism in the step (e) is yeast.

10. The method according to claim 9, wherein the yeast belongs to the genus *Saccharomyces, Schizosaccharomyces, Sporobolomyces, Torulopsis, Trichosporon, Wickerhamia, Ashbya, Blastomyces, Candida, Citeromyces, Crebrothecium, Cryptococcus, Debaryomyces, Endomycopsis, Geotrichum, Hansenula, Kloeckera, Lipomyces, Pichia, Rhodosporidium* or *Rhodotorula*.

11. The method according to claim 10, wherein the yeast belonging to the genus *Saccharomyces* is *Saccharomyces cerevisiae, Saccharomyces baynus* or *Saccharomyces carlsbergensis*.

12. The method according to claim 1, wherein the step (d-2) further comprises a step of pulverizing the solid phase before the sonication of the solid phase.

13. The method according to claim 12, wherein the pulverized solid phase has an average particle diameter from 0.1 mm to 2 cm.

* * * * *